(12) United States Patent
Aherne et al.

(10) Patent No.: US 8,753,328 B2
(45) Date of Patent: Jun. 17, 2014

(54) INTRAVASCULAR CATHETER COMPRISING A REINFORCING MICRO-TAPE

(75) Inventors: Jason Laurence Aherne, Velp (NL); Peter Gerard Akker, Doetinchem (NL)

(73) Assignee: Teijin Aramid B.V., Arnhem (NL)

( * ) Notice: Subject to any disclaimer, the term of this patent is extended or adjusted under 35 U.S.C. 154(b) by 394 days.

(21) Appl. No.: 12/747,421

(22) PCT Filed: Dec. 4, 2008

(86) PCT No.: PCT/EP2008/066749
§ 371 (c)(1),
(2), (4) Date: Jun. 10, 2010

(87) PCT Pub. No.: WO2009/074502
PCT Pub. Date: Jun. 18, 2009

(65) Prior Publication Data
US 2010/0268173 A1   Oct. 21, 2010

(30) Foreign Application Priority Data
Dec. 11, 2007   (EP) ...................................... 07023960

(51) Int. Cl.
*A61M 25/00*   (2006.01)
(52) U.S. Cl.
USPC .......................................................... 604/527
(58) Field of Classification Search
USPC ........................... 604/523, 524, 525, 526, 527
See application file for complete search history.

(56) References Cited

U.S. PATENT DOCUMENTS

| | | | | |
|---|---|---|---|---|
| 4,425,919 A | * | 1/1984 | Alston et al. | 600/435 |
| 4,516,972 A | * | 5/1985 | Samson | 604/526 |
| 4,528,223 A | * | 7/1985 | Kumazawa et al. | 428/34.5 |
| 4,626,306 A | * | 12/1986 | Chabrier et al. | 156/180 |
| 4,997,693 A | * | 3/1991 | Sonoh et al. | 428/46 |
| 5,176,660 A | * | 1/1993 | Truckai | 604/527 |
| 5,234,416 A | * | 8/1993 | Macaulay et al. | 604/527 |
| 5,441,489 A | * | 8/1995 | Utsumi et al. | 604/525 |

(Continued)

FOREIGN PATENT DOCUMENTS

| | | |
|---|---|---|
| EP | 0 316 922 A2 | 5/1989 |
| EP | 0 517 075 A1 | 12/1992 |

(Continued)

OTHER PUBLICATIONS

Co-pending U.S. Appl. No. 12/734,898, filed Jul. 1, 2010, which is a U.S. National phase application of PCT/EP2008/066179.

(Continued)

*Primary Examiner* — Kevin C Sirmons
*Assistant Examiner* — William Carpenter
(74) *Attorney, Agent, or Firm* — Oliff PLC

(57) ABSTRACT

A catheter, such as an intravascular catheter, includes a longitudinally pre-oriented tubular substrate and reinforcing means surrounding and in contact with the substrate, the reinforcing means wound over the substrate, and a tubular superstrate surrounding the reinforcing means forcing the reinforcing means against the substrate and maintaining the reinforcing means wound over the substrate. The reinforcing means is a micro-tape having a width less than 0.5 mm and includes a filament layer having a cross sectional aspect ratio (width/height) of 2 to 20, wherein the filaments are fixated by a cured or solidified resin or wax, which constitutes 2 to 40 wt % of the micro-tape.

6 Claims, 2 Drawing Sheets

(56) References Cited

U.S. PATENT DOCUMENTS

| | | | |
|---|---|---|---|
| 5,472,435 A * | 12/1995 | Sutton | 604/540 |
| 5,538,513 A * | 7/1996 | Okajima | 604/527 |
| 5,674,208 A * | 10/1997 | Berg et al. | 604/527 |
| 5,891,114 A * | 4/1999 | Chien et al. | 604/527 |
| 5,947,940 A * | 9/1999 | Beisel | 604/526 |
| 6,171,297 B1 * | 1/2001 | Pedersen et al. | 604/527 |
| 6,503,193 B1 | 1/2003 | Iwasaki et al. | |
| 6,508,806 B1 * | 1/2003 | Hoste | 604/524 |
| 6,689,120 B1 | 2/2004 | Gerdts | |
| 6,945,956 B2 | 9/2005 | Waldhauser et al. | |
| 7,625,337 B2 * | 12/2009 | Campbell et al. | 600/156 |
| 7,820,565 B2 * | 10/2010 | van Heerden et al. | 442/134 |
| 7,850,675 B2 * | 12/2010 | Bell et al. | 604/523 |
| 7,955,313 B2 * | 6/2011 | Boismier | 604/527 |
| 8,031,996 B2 * | 10/2011 | Willemsen et al. | 385/100 |
| 8,377,035 B2 | 2/2013 | Zhou et al. | |
| 2004/0176740 A1 * | 9/2004 | Chouinard | 604/527 |
| 2005/0059957 A1 * | 3/2005 | Campbell et al. | 604/524 |
| 2005/0061771 A1 * | 3/2005 | Murphy | 216/17 |
| 2006/0020256 A1 * | 1/2006 | Bell et al. | 604/523 |
| 2006/0137156 A1 * | 6/2006 | Kawabe et al. | 28/271 |
| 2006/0229589 A1 | 10/2006 | Itou et al. | |
| 2007/0088323 A1 | 4/2007 | Campbell | |

FOREIGN PATENT DOCUMENTS

| | | |
|---|---|---|
| JP | A-8-71157 | 3/1996 |
| JP | A-2000-296105 | 10/2000 |
| JP | A-2006-515778 | 6/2006 |
| JP | A-2006-288670 | 10/2006 |
| WO | WO 2004/058341 A2 | 7/2004 |

OTHER PUBLICATIONS

International Search Report issued for International Application No. PCT/EP2008/066749 on Jan. 30, 2009.

Written Opinion issued for International Application No. PCT/EP2008/066749 on Jan. 30, 2009.

* cited by examiner

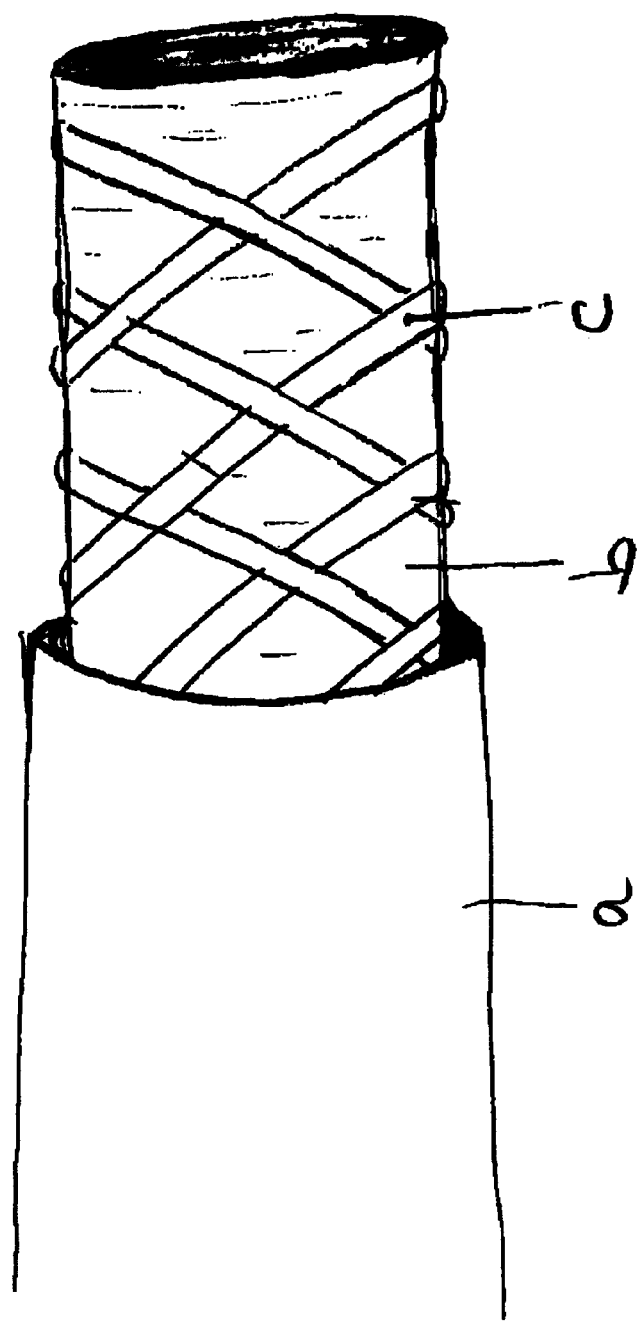

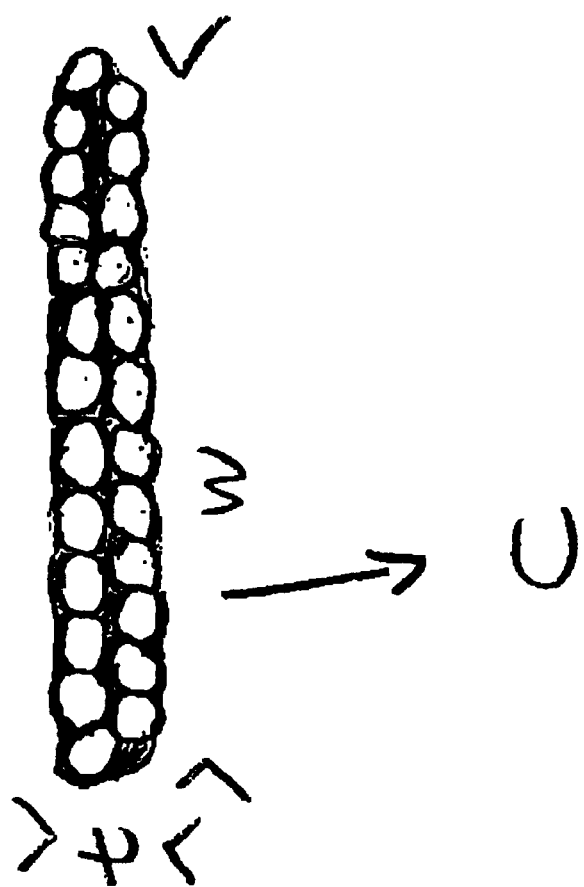

INTRAVASCULAR CATHETER COMPRISING A REINFORCING MICRO-TAPE

This application is a U.S. National Phase Application of PCT Application No. PCT/EP2008/066749 filed Dec. 4, 2008, which claims priority to European Application No. EP 07023960.3 filed Dec. 11, 2007. The disclosure of each of the prior applications is hereby incorporated by reference herein in its entirety.

BACKGROUND

The invention pertains to an intravascular catheter comprising reinforcing means. Catheters comprising reinforcing means are known. Catheters are used in medical diagnostic procedures by inserting them into a patient's body. In order to be able to insert a catheter the catheter must be flexible enough to bend in conformance with the passageways, but also rigid enough to provide torque transmission and adequate support structure for minimizing kinking.

In U.S. Pat. No. 4,425,919 a torque transmitting catheter apparatus including a longitudinally pre-oriented thin-walled tubular substrate surrounded by a thin-walled reinforcing means comprising a flat metal wire braid wound over the substrate has been described. Metal wires provide a good support to substrates of the catheter, but due to the metal such catheters cannot be used for fluoroscopic investigation and MRI scanning the patient.

In EP 0517075 an intravascular catheter such as a guiding catheter of composite construction has been disclosed having an inner tubular member of braided polymeric fibrous strands impregnated with a thermoset polyurethane and having an outer jacket or coating of thermoplastic polyurethane secured to the braided tubular member. This catheter does not contain any metal reinforcing material and therefore is suitable for fluoroscopic investigation and MRI scanning. However, it was found that the reinforcing polymeric fibrous strands do not give sufficient stiffness to the catheter to fully prevent kinking of the catheter when inserted into an artery of a patient.

SUMMARY

It is therefore an object of the present invention to provide a guiding catheter for use in intravascular procedures such as percutaneous transluminal coronary angioplasty (PICA), which has a rigidity comparable with metal reinforcing means to provide good torque transmission and adequate support structure for minimizing kinking, but which are nevertheless microwave inactive to allow MRI scan in patients with inserted catheter.

DETAILED DESCRIPTION

FIG. 1 shows an embodiment of the catheter described herein. This catheter contains superstrate a, substrate b and micro-tape c as reinforcing means.

FIG. 2. shows the micro-tape c of FIG. 1, an example of the micro-tapes described herein. The micro-tape contains filaments and has height t and width w, giving a cross sectional aspect ratio w/t.

To this end the invention relates to an intravascular catheter comprising a longitudinally pre-oriented tubular substrate and reinforcing means surrounding and in contact with the substrate, the reinforcing means wound over the substrate, and a tubular superstrate surrounding the reinforcing means forcing the reinforcing means against the substrate and maintaining the reinforcing means wound over the substrate, characterized in that the reinforcing means is a micro-tape having a width less than 0.5 mm and comprising a filament layer having a cross sectional aspect ratio (width/height) of 2 to 20, wherein the filaments are fixated by a cured or solidified resin or wax, which constitutes 2 to 40 wt % of the micro-tape.

Catheter insertion can induce trauma to the walls of the patient's passageways. In order to minimize this trauma the instant invention, flat cross-section synthetic fibre reinforcement micro-tape have a small overall outside diameter of less than 0.5 mm, preferably less than 0.1 mm. The cross sectional aspect ratio (width/height) of 2 to 20 renders the micro-tape flat. Preferred aspect ratio is within the range 2 to 10.

The highly flexible catheter of this invention which bends in conformance with the passageways minimizes trauma. On the other hand the catheter must be rigid enough to provide adequate torque transmission. Without adequate torque transmission, the catheter cannot be precisely rotated into the desired body organ. Further, poor torque transmission causes buckling, wind-up and whiplash, inducing trauma to the passageways and causing pain and discomfort to the patient. Thus, heretofore the medical profession has been faced with a trade-off between a highly flexible catheter apparatus which fails to perform adequately in torsion or a rigid catheter which creates an intolerable amount of trauma. It was found that micro-tapes made of high performance fibers such as aramid, high modulus polyethylene (HMPE), polyetheretherketone (PEEK), or Thermotropic Liquid Crystal Polymers (TLCP) fibers including polyester-polyarylate fibers show the best balance between optimum torque transmission and kink-resistance.

The instant invention solves this dilemma by providing a thin wall reinforcing means comprising a flat synthetic fiber micro-tape. The micro-tape can be braided or spiralized over a longitudinal pre-oriented substrate which adequately supports the reinforcing means. The braid or spiral is maintained in place by a surrounding superstrate. Using this structure the instant invention has extremely good torque transmission characteristics while maintaining superior flexibility and kink-resistance. Because the instant invention includes a pre-oriented substrate, extremely thin walls are possible. This allows the overall outside diameter to be minimized while maximizing the inside diameter. In one example this allows adequate diagnostic fluid to flow though the substrate thereby enabling the x-ray or MRI machine or the like to properly photograph the desired passageway.

Examples of aramid are poly-paraphenylene terephthalamide (PPTA) which is sold as TWARON® and KEVLAR® and co-poly-(paraphenylene/3,4'-oxydi-phenylene terephthalamide which is sold as TECHNORA®. Also PPTA copolymers, for instance made from PPD monomers including Cl-PPD. MeO-PPD, DAPBI and the like, are suitable as aramid filaments. Other rigid rod polymers such as PBO, which is sold as ZYLON®, and PIPD, which is also known as M5, are also suitable.

Examples of HMPE are high modulus polyethylenes obtainable under the trade names such as DYNEEMA®, MARLEX®, PLEXAR®, DOWLEX®, ETHYLUX®, HALENE®, HIPLEX®, HOSTALEN®, SPECTRA® and the like.

Examples of PEEK are polyetheretherketones that are obtainable under the trade names VICTREX®, GATONE®, KETRON®, KETASPIRE® and the like.

An example of a polyester-polyarylate is known under the trade name VECTRAN®. The substrate and superstrate that are used are the substrates and superstrates that are commonly used in catheters. For instance, the preferred substrates and superstrates may be made from, but are not limited to, polymeric materials such as polyethylene, polyamide, polyimide, polytetrafluoroethylene (PTFE), and polyurethane.

The micro-tapes of the invention comprise filaments fixated by a cured or solidified resin, wherein the width/height ratio of the micro-tape is 2 to 20, preferably 2 to 10.

The micro-tapes can be prepared as described in co-pending patent application EP 07023191.5 Thus by this method a flexible fibrous micro-tape containing 60 to 98 wt % fiber based on the weight of the micro-tape, is made from multifilament yarn comprising the steps:

a1) spreading the filaments of the yarn to obtain a filament layer having a cross sectional aspect ratio (w/h) of 2 to 20; and
b1) treating the spread filaments with a curable resin, or a liquid thermoplastic resin or wax; or
a2) treating the yarn with the curable resin, or the liquid thermoplastic resin or wax; and
b2) spreading the filaments of the yarn to obtain a filament layer having a cross sectional aspect ratio (w/h) of 2 to 20; followed by
c) fixating the filaments by curing or solidifying the resin to obtain the micro-tape.

It is desirable that the fibers after having undergone spreading of the filaments are fixated as soon as possible to prevent entangling of the filaments and fluffing, and to maintain its required dimensional properties (such as width and height). This object is obtained by using other curable, liquid thermoplastic resins or liquid wax, and after being cured or solidified will fixate (immobilize) the filaments permanent. It is therefore desirable that the curing or solidifying process is performed as quickly as possible. Most of the resins of the prior art are unsuitable for such quick fixation. Curable resins are particularly preferred since these can quickly be hardened, thereby trapping the filaments to fixation. In principle both heat- and radiation-curing (such as UV and electron beam curing) can be used. Heat curing can preferably be performed with thermoset resins (suitable examples include among others epoxy, vinyl ester, unsaturated polyester, polyurethane, and phenolic resins). In a convenient method the spread filaments are led through a bath, a die, or an applicator, containing curable resin, and then led to heated rollers, a hot-air oven, a hot-plate, or a combination thereof, on which the resin quickly cures, thereby fixating the filaments. In another embodiment when using liquid thermoplastic resin, the spread filaments are led through a bath, a die, or an applicator, and then led to cooled rollers to obtain quick solidification of the resin. If so required the yarn may be dried, for example after having performed process step b1) or a2).

Even more conveniently radiation-curable resin is applied onto the spread filaments. Suitable radiation-curable resins are for example resins containing allyl, vinyl, or (meth)acrylate functionality. These resin treated filaments are immediately led into an irradiation area, such as an area with a UV lamp or in an electron beam area, under which conditions the resin instantaneously cures. The fast curing allows high processing speeds, which makes UV-curing commercially attractive. For instance, in-line application and UV-curing can be considered as a post-treatment step in a high-speed spin-line up to 700 m/min.

In another convenient method the yarn bundle is treated with a liquid thermoplastic resin or wax. A liquid thermoplastic resin or wax is a thermoplastic resin or wax that is liquid by being beyond its melting point, or by dissolution or emulsification in a solvent. These materials solidify by lowering the temperature to below their melting point, or by removing the solvent, for instance by evaporation. Suitable solvents are water or common organic solvents such as toluene, isohexadecane, ethanol, acetone, ether and the like. More convenient is a method in which the yarn bundle is treated with a low viscous aqueous solution or dispersion of the thermoplastic resin or wax. The low viscous aqueous dispersion quickly penetrates in the yarn bundle and spreads out the resin or wax over the filaments. Next, the water phase is completely or partly removed by contact-less heating in, for example, a hot air oven and the yarn bundle is spread using one or more rods. Immediately after the rods, the spread yarn is further heated to evaporate the rest amount of water and/or to fixate the thermoplastic resin on the surface of a hot roller, such as for example a hot godet. A second godet can be used to allow an easy winding of the flexible micro-tape. In case a dispersion of molten wax or thermoplastic resin is used, it is preferred that after the rod spreading step, the yarn is lead over a cold roller to fixate the filaments in the micro-tape.

To obtain flexible micro-tapes with maximum compression modulus it is desirable to apply as low as possible amounts of resin. The micro-tapes do contain at least 60 wt % fiber, more preferably at least 70 wt % (based on the weight of the micro-tape), and when a UV-curable resin or wax is used, preferably at least 80 wt % is fiber. When using thermoplastic resins even higher quantities of fiber are satisfactory, and preferably at least 90 wt % fiber is used, i.e., less than 10 wt % resin or wax. The tensile strength and the compression stiffness of these filament micro-tapes are better than for steel wire-containing tapes.

The invention is further illustrated by the following non-limitative examples.

Example 1

TECHNORA® HMY T 242 (61 dtex/f25) is subjected to the following treatments. The yarn is rollingly unwound. The yarn then passes a device to dampen away the tension fluctuations, caused by the unrolling of the yarn. Successively, the yarn passes yarn tension monitor F1, non heated godet 1, yarn tension monitor F2, plate, yarn tension monitor F3, non heated godet 2 and yarn tension monitor F4. Application of the tested aqueous finishes (see table 5) takes place after tension meter 4 and before entrance of the first tube oven. The tested aqueous finishes are applied by means of a ceramic applicator fed by a glass syringe pump. After the heated first tube oven (intended to evaporate the solvent) a non heated godet 2 and a yarn tension meter F5 is passed. Next the finished yarn passes (non heated) tube oven 2 and non heated godet 3. By applying high yarn tension (tension monitor F5) between the non-heated godet 4 and the heated godet 5 the yarn is shaped on hot godet 5 into a tape form. After passing the heated godet 5, the yarn is allowed to cool down (under tension (monitor F7)) before winding.

In Tables 1 and 2, respectively, the used finishes and the process conditions/characteristics are mentioned.

TABLE 1

| Used aqueous finishes | | | |
|---|---|---|---|
| Product name | Entry | Supplier | Composition |
| Alberdingk Boley U400N | 1 | Alberdingk Boley | polyether-polyurethane dispersion |
| Schlichte LB 100 | 6 | Eastman Chemical Company | Water dispersible polymer (sulfonated polyester) |

TABLE 2

| | Experiment no. | |
|---|---|---|
| | 1 | 2 |
| Yarn speed (m/min) | 4 | 4 |
| Used finish | Entry 1 as a 20 wt % aqueous dispersion | Entry 6 as a 20 wt % aqueous solution |
| solid content dosed onto the yarn in wt % | 22 | 30 |
| Application rate (ml/min) | 0.027 | 0.036 |
| Yarn tensions F1/F2/F3/F4/F5/F6/F7 (cN) | 46/69/88/61/ 104/640/310 | 50/68/90/106/ 134/640/310 |
| Temperature 1$^{st}$ oven (3 sections) | 160° C./160° C./ 200° C. | 160° C./160° C./ 200° C. |
| Temperature 2$^{nd}$ oven (3 sections) | —/—/— | —/—/— |
| Godet 1-4, temperatures | — | — |
| Wraps on godets 1-4 | 5 | 5 |
| Wraps on heated godet 5 | 5 | 5 |
| Godet 5, temperature (° C.) | 170 | 170 |
| Winding tension (cN) | 260 | 260 |
| Produced flexible microtape: | | |
| width (mm) | 0.1 | 0.15 |
| height (mm) | 0.036 | 0.024 |
| width/height ratio | 2.8 | 6.3 |
| Fiber content of micro-tape in wt % | 82 | 77 |

The invention claimed is:

1. A catheter, comprising:
   a longitudinally pre-oriented tubular substrate,
   a reinforcing tape surrounding and in contact with the substrate, the reinforcing tape being wound over the substrate, and
   a tubular superstrate surrounding the reinforcing tape, the tubular superstrate forcing the reinforcing tape against the substrate and maintaining the reinforcing tape to be wound over the substrate,
   wherein the reinforcing tape consists of a micro-tape having a width less than 0.1 mm and having a filament layer consisting of filaments, the filament layer having a cross sectional aspect ratio (width/height) of from 2 to 20,
   wherein the filaments are selected from the group consisting of aramid, high modulus polyethylene, polyetheretherketone, and polyester-polyarylate,
   wherein the micro-tape includes only flat strands,
   wherein the micro-tape includes a fiber content of at least 77 wt %, and
   wherein the filaments are fixed by a cured or solidified resin or wax, comprising from 2 to 23 wt % of the micro-tape.

2. The catheter of claim 1,
   wherein the catheter is an intravascular catheter.

3. The catheter of claim 2,
   wherein the micro-tape is wound over the substrate as a braid.

4. The catheter of claim 2,
   wherein the micro-tape is spirally wound over the substrate.

5. The catheter of claim 1,
   wherein the micro-tape is wound over the substrate as a braid.

6. The catheter of claim 1,
   wherein the micro-tape is spirally wound over the substrate.

* * * * *

UNITED STATES PATENT AND TRADEMARK OFFICE
CERTIFICATE OF CORRECTION

PATENT NO. : 8,753,328 B2  
APPLICATION NO. : 12/747421  
DATED : June 17, 2014  
INVENTOR(S) : Aherne et al.

Page 1 of 1

It is certified that error appears in the above-identified patent and that said Letters Patent is hereby corrected as shown below:

In the Specification

Col. 1, line 46, delete "percutaneous transluminal coronary angioplasty (PICA)" and insert --percutaneous transluminal coronary angioplasty (PTCA)--.

Col. 4, line 49, delete "By applying high yarn tension (tension monitor F5)" and insert --By applying high yarn tension (tension monitor F6)--.

Signed and Sealed this  
Second Day of September, 2014

Michelle K. Lee  
*Deputy Director of the United States Patent and Trademark Office*